United States Patent [19]

Ibbotson

[11] 4,014,935
[45] Mar. 29, 1977

[54] CARBODIIMIDES

[75] Inventor: Arthur Ibbotson, Manchester, England

[73] Assignee: Imperial Chemical Industries Limited, London, England

[22] Filed: Mar. 25, 1976

[21] Appl. No.: 670,155

[30] Foreign Application Priority Data

| Apr. 3, 1975 | United Kingdom | 13656/75 |
| Apr. 3, 1975 | United Kingdom | 13657/75 |
| Apr. 3, 1975 | United Kingdom | 13658/75 |
| Apr. 3, 1975 | United Kingdom | 13659/75 |
| Apr. 16, 1975 | United Kingdom | 15649/75 |
| Oct. 30, 1975 | United Kingdom | 44965/75 |

[52] U.S. Cl. .......................... 260/566 R; 252/426
[51] Int. Cl.$^2$ .................................... C07C 119/00
[58] Field of Search ............... 260/551 CD, 566 R; 252/426

[56] References Cited

UNITED STATES PATENTS

| 2,840,589 | 6/1958 | Smeltz | 260/453 |
| 3,056,835 | 10/1962 | Monagle et al. | 260/551 CD |
| 3,907,780 | 9/1975 | Hughes | 260/453 |

FOREIGN PATENTS OR APPLICATIONS

| 1,356,851 | 6/1974 | United Kingdom | 260/453 |

*Primary Examiner*—Gerald A. Schwartz
*Attorney, Agent, or Firm*—Cushman, Darby & Cushman

[57] ABSTRACT

A process for the conversion of isocyanate groups in a refined organic isocyanate into carbodiimide groups which comprises heating said organic isocyanate with a catalyst of the formula:

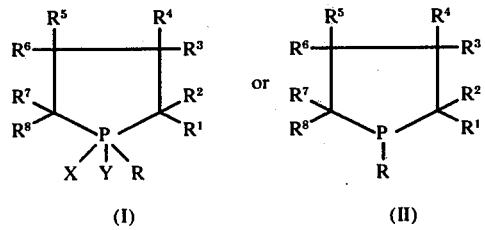

or the 2,3 or 3,4-mono-unsaturated analogues thereof, wherein R is an optionally substituted hydrocarbyl group, $R^1$ to $R^8$ which may be the same or different are hydrogen, chlorine or lower alkyl, X and Y may be chlorine or bromine or X and Y taken together may represent the divalent atoms =O or =S or the divalent radial =N aryl, followed by deactivation of the catalyst by adsorption on a substrate or by addition of one or more of the halides of hydrogen, phosphorus or tin or an oxyhalide of phosphorus or sulphur. When only partial conversion takes place the carbodiimides react with further isocyanate groups to give uretonimines. The products are useful for the manufacture of polymers especially microcellular polyurethanes.

19 Claims, No Drawings

CARBODIIMIDES

This invention relates to the conversion of isocyanate groups in organic isocyanates into carbodiimide groups in the presence of certain types of phosphorus containing catalysts and to the deactivation of the effect of such catalysts after the desired degree of reaction has been achieved. The invention also relates to the further reaction of such carbodiimide groups with isocyanate groups remaining in the organic isocyanate after completion of the desired carbodiimide-forming reaction.

It is known that organic isocyanates can be converted to carbodiimides by heating at elevated temperatures, the reaction involving the evolution of carbon dioxide, i.e.

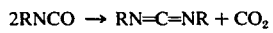

$$2RNCO \rightarrow RN{=}C{=}NR + CO_2$$

A variety of phosphorus-containing catalysts have been proposed for the conversion of isocyanate groups in organic isocyanates into carbodiimide groups.

One class of such catalysts is that comprising amongst others the trialkyl phosphate and phosphoramide types, for example, triethyl phosphate and hexamethyl phosphoramide. This class of catalyst is active at high temperature, for example over 150° C, but has little or no activity at room temperature, for example. For this reason, this class of catalyst has been used in cases where only partial conversion of isocyanate groups to carbodiimide groups is required and after conversion at high temperatures, cooling, and storage at room temperature, has been found to provide sufficient deactivation of the catalyst, without chemical deactivation, to give acceptable long term storage stability to the product.

However, operation of high temperature processes, apart from being expensive in energy terms, is hazardous due to possible polymerisation of the isocyanate.

A second class of catalysts for the isocyanate to carbodiimide conversion process are catalysts which are active at much lower temperatures than those mentioned above and therefore preferable in that they avoid use of high temperature with its attendant hazards. This second class based on the pholidine or phospholene nucleus are however sufficiently active at room temperature as to affect the stability of a product which still contains free isocyanate groups, for this reason they have to be deactivated by chemical or other means.

Boron trifluoride etherate has been proposed for the deactivation of such catalysts of the phospholidine or phospholene type and although addition of this deactivator improves the stability of products containing carbodiimide and isocyanate groups, and uretoimine groups formed therefrom, it is not entirely satisfactory in this respect.

We have now found that such phospholene and phospholidine type catalysts may be deactivated by new methods superior in efficiency to the known method using boron trifluoride etherate and giving products of considerably enhanced stability.

Thus according to the present invention there is provided a process for the conversion of isocyanate groups in a refined organic isocyanate into carbodiimide groups which comprises heating said organic isocyanate with a catalyst of the formula

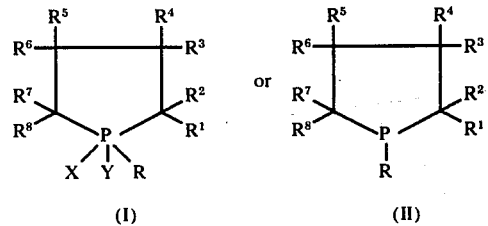

or the 2,3 or 3,4-mono-unsaturated analogues thereof, wherein R is an optionally substituted hydrocarbyl group, $R^1$ and $R^8$ which may be the same or different are hydrogen, chlorine or lower alkyl, X and Y may be chlorine or bromine or X and Y taken together may represent the divalent atoms $={O}$ or $={S}$ or the divalent radical $={N}$ aryl, followed by deactivation of the catalyst by adsorption on a substrate or by addition of one or more of the halides of hydrogen, phosphorus or tin or an oxyhalide of phosphorus or sulphur.

By the term lower alkyl used in this specification we mean alkyl having from 1 to 4 carbon atoms.

In referring to the 2,3 and 3,4-mono unsaturated analogues in the above definition of the catalysts it will be appreciated that we are referring to compounds of formula

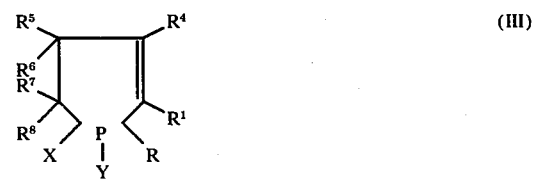

and

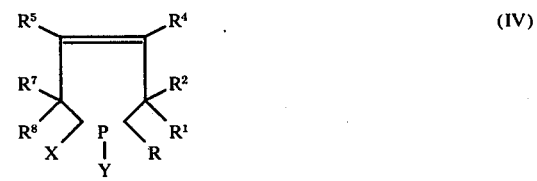

wherein the various R, X and Y groups are as above defined, and also to the related compounds wherein X and Y are absent.

In respect of the catalysts formulated hereinbefore, examples of R include methyl, ethyl, propyl, isopropyl, n-butyl, tert-butyl, cyclohexyl, n-dodecyl, phenyl, o-, m- or p-tolyl, xylyl, naphthyl, 4-diphenyl, 2-phenylethyl, 2-chloroethyl, 2-methoxyethyl, o-, m- or p-chlorophenyl, p-methoxyphenyl and p-N,N-dimethylaminophenyl.

As examples of $R^1$ and $R^8$, which may be the same or may be different, there may be mentioned hydrogen, chlorine, methyl, ethyl, propyl, isopropyl and butyl, a preferred lower alkyl group is methyl.

As examples of X and Y, which may be the same or different, there may be mentioned chlorine and bromine.

As examples of X and Y taken together there is mentioned the divalent atoms $O{=}$ and $S{=}$ and also the divalent radical $={N}$ aryl examples of which include phenylimino, p-tolylimino and $={N}$-tolylene-$N{=}V$ and =N-phenylene-N=V where V is a residue of formula (I) linked through the XY positions.

Specific examples of catalysts which may be used in the present process include 1-phenyl-3-methyl phospholene oxide
1-benzyl-3-methyl phospholene oxide
1-ethyl-3-methyl phospholene oxide
1-phenyl-3-methyl phospholene dichloride
1-benzyl-3-methyl phospholene dichloride
1-ethyl-3-methyl phospholene dichloride
1-phenyl-3-methyl phospholene sulphide
1-benzyl-3-methyl phospholene sulphide 1-ethyl-3-methyl phospholene sulphide
1-phenyl-1-phenylimino-3-methyl phospholene oxide
1-benzyl-1-phenylimino-3-methyl phospholene oxide
1-ethyl-1-phenylimino-3-methyl phospholene oxide
1-phenyl phospholidine
1-benzyl phospholidine
1-ethyl phospholidine
1-phenyl-3-methyl phospholene oxide.

Preferred catalysts are compounds of Formulae III or IV or mixtures thereof wherein R is phenyl, $R^1$, $R^2$, $R^5$, $R^6$, $R^7$ and $R^8$ are hydrogen, $R^4$ is methyl or chlorine especially methyl and X and Y are as hereinbefore defined. Preferably X and Y together represent a divalent oxygen atom.

A particularly preferred catalyst is 1-phenyl-3-methyl phospholene oxide.

The amount of catalyst used in the process of the invention may vary widely according to the particular catalyst and the desired rate and degree of conversion of the isocyanate groups.

It is a particular feature of this invention that only very small quantities of catalyst are required in this invention. Thus whilst amounts from 1 ppm to as high as 100 ppm may be employed, we find best results to be achieved using considerably less for example less than 25 ppm and preferably less than 10 ppm when an isocyanate having low acidity is employed.

Catalysts for use in the present invention may be made by known methods, thus for example those wherein X and $X^1$ are halogen may be made by direct addition of a dichloride to a 1,3-diene, viz:

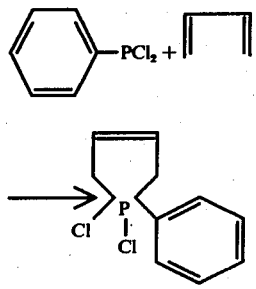

The oxide and sulphide may be made from this chloride by hydrolysis or reaction with sodium sulphide. The phospholenes may be obtained by dehalogenation by reaction with magnesium.

Phosphinimines may be prepared by the reaction of phosphines with the appropriate azide. Isomerisation of the double bond in the ring may take place during these reactions.

Compounds in which the ring is saturated may be conveniently made by adding chlorine to the reaction products of, for example, the Grignard reagent from 1,4-dichlorobutane and phenyldichlorophosphine, i.e. $ClMg(CH_2)_4MgCl$

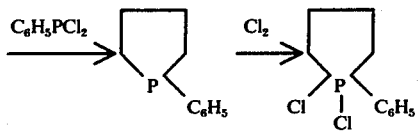

Any monofunctional or polyfunctional refined organic isocyanate may be treated by the process of the present invention.

By the term refined we mean an isocyanate which has been subjected to a purification process such as distillation or crystallisation or a combination of such processes.

Examples of such isocyanates include phenyl isocyanates, tolyl isocyanates, chlorophenyl isocyanates, naphthyl isocyanates, tolylene-2,4 and 2,6-diisocyanates and mixtures thereof, p-phenylene diisocyanate, chlorophenylene diisocyanates, 4,4'-diphenylmethane diisocyanate and mixtures of this isomer with other isomers thereof and hexamethylene diisocyanate.

The invention is particularly useful when applied to aromatic polyisocyanates, i.e. those having two or more isocyanate groups. Examples of such isocyanates include tolylene diisocyanates especially the well-known commercially available mixtures of the 2,4- and 2,6-isomers thereof and diphenylmethane diisocyanates. Mixtures of polyisocyanates, for example, tolylene diisocyanate and diphenylmethane diisocyanate may also be used.

Refined, i.e. distilled or crystallised, diphenylmethane diisocyanates are solids melting about 40° C and the invention is particularly applicable to such isocyanates, as conversion of a proportion of the isocyanate groups in such diisocyanates to carbodiimides gives liquefied compositions of the said diisocyanates which are particularly useful in polyurethane formulations in that they can be incorporated at room temperature without the difficulties inherent in their incorporation as solids or above the melting point.

The application of the present process could result in the conversion of all the isocyanate groups in an isocyanate to carbodiimide groups, the process however has been found particularly useful for the conversion of only a proportion of the isocyanate groups. In the case of diisocyanates and higher polyisocyanates the process is valuable for the conversion of from 3% to 35% of the isocyanate groups to carbodiimide groups. This use of the present process is of value for introducing into the isocyanate, uretonimine groups which are formed as adducts of a carbodiimide group and an isocyanate group.

Uretonimine groups are produced by reacting an isocyanate group with a carbodiimide group and may be easily introduced into an isocyanate composition by converting some of the isocyanate groups to carbodiimide groups by the present process and then allowing the carbodiimide groups to react with unreacted isocyanate groups to form uretonimine groups.

Formation of a uretonimine takes place as follows:

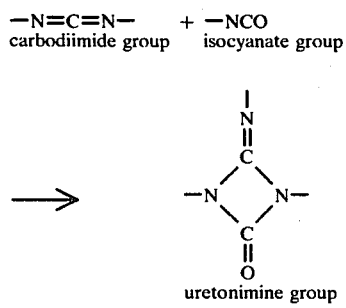

The reaction is reversible and the adduct tends to split into carbodiimide and isocyanate on heating to elevated temperature.

Once carbodiimide groups have been introduced into an isocyanate composition, reaction between carbodiimide groups and isocyanate groups takes place with formation of uretonimine groups. In order to permit this reaction to proceed to near completion it is normally necessary to allow the isocyanate/carbodiimide reaction mixture to stand for a time at room temperature for the uretonimine-forming reaction to take place. Conversion to uretonimine may not go to absolute completion and there sometimes remains in the composition a small amount of carbodiimide which is not converted to uretonimine despite the presence of excess isocyanate groups.

Thus the present process may be used for the introduction of a number of carbodiimide groups into a polyisocyanate composition and the product allowed to stand to convert at least a proportion of such groups to uretonimine groups by further reaction. The final products containing a proportion of uretonimine groups are useful as polyisocyanate compositions for the manufacture of polyurethane foams particularly those of the microcellular type often known as microcellular elastomers, having a valuable range of properties.

In carrying out the process of the invention the catalyst, either alone or in an organic solvent inert to isocyanates, is added to the isocyanate and the mixture heated to the desired reaction temperature for a length of time sufficient to achieve the desired degree of conversion of isocyanate groups to carbodiimide groups. The time and temperature are clearly interdependent in obtaining a desired degree of conversion. In respect of temperature it is preferred to operate below 150° in order to minimise side reactions, for example dimerisation which can result in deposition of sediment on storage of the product. A temperature of from 80° C to 140° C has been found convenient and the lower the temperature the lower the rate of dimer formation.

Inert organic solvents which can be used for incorporating the catalyst include chlorinated hydrocarbons such as methylene dichloride, perchloroethylene and monochlorobenzene, and ethers such as dibutyl ether and glycol bis-ethers.

On completion of the desired degree of reaction of isocyanate group the catalyst is deactivated.

Deactivation may be carried out by absorption of the catalyst on a substrate followed by removal of the substrate by physical means or by the addition of one or more of the halides of hydrogen, phosphorus or tin or an oxyhalide of phosphorus or sulphur.

When deactivating the catalyst by the use of a substrate the reaction mixture is treated with a solid adsorbent substrate, optionally after cooling to room temperature.

Solid adsorbent substrates which may be used include siliceous earths and adsorbent carbons and metal oxides and salts.

Specific examples of such substrates include charcoal, activated carbon, silica, alumina, complex silicates such as clays, kieselguhr, bentonite, Fuller's earth and zeolites. Siliceous earths are particularly valuable adsorbents.

Treatment of the reaction mixture with the substrate may be carried out by agitating the substrate in the reaction mixture for a short period of time for example 1 minute to several hours. Treatment may be carried out at any convenient temperature preferably between room temperature and the reaction temperature used to make the product.

Removal of the solid absorbent substrate from the reaction mixture may be accomplished by decantation, filtration or centrifuging.

Treatment may be effected by a batchwise process or if desired may be effected continuously.

Neither the catalyst nor the substrate interfere with the formation of uretonimine groups by reaction of isocyanate with carbodiimide groups.

When the catalyst is deactivated by the addition of a halide of hydrogen, phosphorus or tin, examples of such deactivators which may be used include hydrogen chloride, hydrogen bromide, phosphorus trichloride, phosphorus pentachloride, tin tetrachloride, tin tetrabromide and tin bromotrichloride.

When the catalyst is deactivated by the addition of an oxyhalide of phosphorus or sulphur, examples of such deactivators include thionyl chloride, sulphuryl chloride and phosphorus oxychloride.

Before adding a chemical deactivator the reaction mixture may be cooled to room temperature but this is not essential.

Chemical deactivators may be used in any convenient amount to provide the deactivating effect. Preferably they are used in an amount of from one to thirty moles of deactivating agent to each mole of catalyst used.

Once deactivation has taken place neither the catalyst nor the deactivator are required for, or interfere with, the reaction of carbodiimide groups with isocyanate groups to give uretonimine groups.

Deactivation by adsorption is in general a superior method of deactivation in giving a product of greater thermal stability but chemical deactivation is adequate, simpler and more attractive in that it does not require additional plant items such as separation or filtration apparatus. For this latter reason chemical deactivation is preferred for simplicity of operation.

Thionyl chloride is a preferred deactivator.

In achieving a certain degree of conversion of isocyanate group to carbodiimide groups, conversion can be carried out as hereinbefore described and the conversion stopped by deactivation when the isocyanate group content has dropped to the desired level as determined by known analytical procedures. Alternatively the conversion can be carried out beyond the desired final level and the product blended with a further amount of the refined isocyanate to give a product having a final total of the desired number of unconverted isocyanate groups. Thus if a product in which 15% of the isocyanate groups have been converted to carbodiimide groups and thence to uretonimine, is required, 20% say of the isocyanate groups can be converted to carbodiimide and the product diluted with further refined diisocyanate until the desired product having 15% of the total isocyanate group is obtained. This can simplify the operation in that instead of constantly monitoring the isocyanate group content during conversion, the conversion can be carried on for a given length of time, conversion stopped, the isocyanate content determined and the product diluted to the required isocyanate value.

Most refined commercial organic isocyanates have a greater or lower degree of acidity and this can vary with different production batches or deliveries of isocyanate. We have, however, found that the effects of isocyanate acidity can be overcome in the present process by incorporating an acid acceptor in the isocyanate in addition to the catalyst.

Thus as a further embodiment of the present invention there is provided a process in which an acid acceptor is incorporated in the reaction mixture.

Any known acid acceptor may be used in the present process, examples include metal oxides, metal salts of weak acids, acrylonitrile, acrylamides, acrylates, carbodiimides and isoureas. The metal oxides are however inconvenient being solids that in general are not readily soluble in isocyanates, their salts with weak acids, although much more soluble, suffer from the disadvantage that they promote unwanted side reactions, for example, trimerisation. The unsaturated compounds, for example acrylonitrile, are often malodorous, of low flash point, and not especially active. The carbodiimides are toxic, unstable or expensive and the isoureas, though active, are not readily available. A preferred class of acid acceptors are the 1,2-epoxides such as glycidol, epichlorohydrin and phenyl glycidyl ether.

The amount of acid acceptor employed is preferably less than 1% by weight of the isocyanate and quite major acceleration in rate is achieved using as little as 0.05% even with a commercial pure isocyanate. Ideally it is preferred to use an amount of acid acceptor corresponding to at least one equivalent for each gram-molecule of acidity present in the isocyanate.

The acid acceptor is incorporated in the isocyanate either before, after or with the catalyst.

A further advantageous feature of the use of an acid acceptor is that the acidity of the product is less than that of the parent isocyanate so that less interference occurs or subsequent use of the product in the manufacture of polyurethanes by base catalysed processes.

Compositions made using the present process are more stable to storage at room temperature and are more thermally stable at for example temperatures of up to 80° C.

The products of the present process are useful for the manufacture of polymers and in particular those products which have isocyanate groups present in addition to carbodiimide and/or uretonimine groups are valuable intermediates for the manufacture of polyurethanes.

The products are particularly useful for the manufacture of microcellular elastomers in particular they give reduced mould or jig occupation times.

The invention is illustrated by the following Examples in which all parts and percentages are by weight except where otherwise stated.

EXAMPLE 1 (preparation of the carbodiimide group-containing isocyanate)

4,4'-Di-isocyanatodiphenylmethane (2000 parts) was mixed with 5 ppm of 1-phenyl-3-methyl-2-phospholene-1-oxide and heated at 125°–130° C for approximately 90 minutes. After cooling to 60° C the concentration of isocyanate groups was 27.35%. Further diisocyanate was added (1068 parts) to raise the isocyanate strength to 29.35%. This product was water white, clear and of acidity 24 ppm. It had a dimer content of 1.42%.

EXAMPLE 1A (Comparative)

The product of Example 1 was heated out of contact with air at 80° C. After 9 days it was viscous and its strength was 23.33% isocyanate groups.

EXAMPLE 1B

The product of Example 1 was stirred with filtercel (2%) (a siliceous earth) for 2 hours at 50° C. After filtering and heating for 9 days at 80° C as in 1A the isocyanate content of the product was still 28.4%.

EXAMPLE 1C

Repeating Example 1B and using Ambosol in place of Filtercel the isocyanate content was 28.45% showing negligible loss in strength.

EXAMPLE 1D

Repeating Examples 1B using Actibon "S" (an activated carbon) in place of Filtercel the isocyanate content similarly fell by only 1% in 6 days at 80° C.

Repeating Example 1B using fumed silica in place of Filtercel the isocyanate content fell to 28.2%.

EXAMPLE 2

Example 1 was repeated using 25 ppm catalyst in the isocyanate and using a reaction time of 6 hours 15 minutes at 60°–82° C. The product was a water white mobile liquid of dimer content 0.73% and isocyanate group content 29.1%. After standing for 5 days the isocyanate content fell to 28.4%.

EXAMPLE 2A

The product of Example 2 was stirred with 2% of Filtercel for 2 hours at 50° C. After filtering and heating at 80° C for 3 days the strength only fell to an isocyanate content of 27.95%.

In the absence of the Filtercel treatment this product was solid after heating 3 days at 80° C.

EXAMPLE 3

4,4'-diisocyanatodiphenylmethane (250 parts) was heated at 80° C in dry nitrogen with 100 ppm (0.025 part) of 1-phenyl-3-methylphospholene oxide. Carbon dioxide was evolved and uretonimine residues were detected in the infra-red spectrum. Analysis by di-n-butylamine titration indicated that the strength in terms of isocyanate content had fallen from 33.6% to 28.7%. This product was divided to permit several experiments on stabilisation or catalyst deactivation.

A. Holding this product without addition of deactivator for 24 hours at 50° C resulted in a fall in isocyanate value to 22.6% showed that efficient deactivation is essential if a product of satisfactory storage stability is to be achieved.

B. Adding thionyl chloride at the rate of 2 moles/mole of phospholene oxide catalyst provided a clear yellow liquid, which after 2 days at 50° C had an NCO content of 28.3, which after a further 24 hours at 80° C was 27.9%.

C. In an identical experiment addition of phosphorus pentachloride gave a water white liquid which had an isocyanate content of 28.25% after 2 days at 50° C and 24 hours at 80° C.

D. Using boron trifluoride etherate as deactivator the isocyanate content of the product fell to 26.5% after only 2 days at 50° C, showing it to be inferior in performance as a deactivator to the deactivators of this invention.

EXAMPLE 4

Pure 4,4'-diisocyanatodiphenylmethane (500 parts) was mixed with 1-phenyl-3-methylphospholene-1-oxide (0.0125 parts) and heated at 80° C for 5 hours after which time the isocyanate value was found by titration with di-n-butylamine to be 27.2%. To 25 parts of this product was added 0.424 parts of a 1% solution of tin tetrachloride in perchloroethylene and the mixture heated for 90 hours at 80° C. The isocyanate group content of the liquid was then 26.1%. In the absence of tin tetrachloride the original product became an intractable solid on heating in this manner.

EXAMPLE 5

A distilled sample of diphenylmethane diisocyanate containing less than 10% of the 2,4'-isomer and over 90% of the 4,4'-isomer and an acidity of ca. 200 ppm of hydrogen chloride was prepared by partial distillation of diisocyanate from a crude phosgenation product containing diphenylmethane diisocyanate and analogues of higher functionality obtained by phosgenation of an aniline/formaldehyde condensate.

To 250 parts of this product was added at 100° C 1-phenyl-3-methyl-2-phospholene-1-oxide (25 ppm by weight of the isocyanate) and the solution stirred for 5 hours. Analysis by titration with di-n-butylamine showed that the isocyanate content had fallen from 33.6% to 29.6%. The experiment was repeated in the presence of a number of acid acceptors used at the rate of 1 molecule of acid acceptor per equivalent of hydrogen chloride present in the isocyanate with the results shown in the Table. At the end of the reaction the catalyst was deactivated by the addition of thionyl chloride.

| Example | Acid Acceptor | Isocyanate content after 5 hours |
|---|---|---|
| 5 | None | 29.6% |
| 6 | Calcium 2-ethylhexoate | 28.6% |
| 7 | Phenylglycidyl ether | 28.1% |
| 8 | 1,2-Propylene oxide | 27.9% |
| 9 | Epichlorohydrin | 25.9% |
| 10 | 1,3-di-p-tolyl-2-methylisourea | 25.2% |

These results show the rate of reaction is accelerated by the use of an acid acceptor.

EXAMPLE 11

Example 5 was repeated using twice the amount of epichlorohydrin acid acceptor that is required to react with the hydrogen chloride present when instead of requiring 5 hours to reach a strength as NCO of 29.6% this level was attained in 2 hours. Comparison of the kinetic curves shows that using only one equivalent of epichlorohydrin (as in Example 5) the isocyanate content after 2 hours was 31.2%, clearly showing that under the stated conditions the reaction rate is increased by using more than the theoretical quantity of epichlorohydrin to react with the hydrogen chloride present in the isocyanate.

EXAMPLE 12

4,4'-Diisocyanatodiphenylmethane of acidity of 50 ppm was mixed with 5 ppm of 1-phenyl-3-methylphospholene-1-oxide and epichlorohydrin (in an amount of 2 moles per mole of acidity present) and heated at 105°–115° C until the isocyanate group content had fallen to 26.9%. This took ca. 4 hours.

A. 55 Parts of this uretonimine modified pure diphenylmethane diisocyanate were blended with 45 parts of 4,4'-diisocyanatodiphenylmethane diisocyanate containing 8.0% of the 2,4'-isomer thereof and containing 195 ppm hydrogen chloride to give a water white liquid blend of viscosity 30.6 centipoises, the hydrogen chloride in the added isocyanate deactivating the catalyst.

The isocyanate content only fell from 29.5% to 28.5% on heating at 80° C for 360 hours.

B. A further 55 parts of the uretonimine modified diisocyanate of Example 12 were blended with 45 parts of a distilled diisocyanate containing 80% of 4,4'-diisocyanatodiphenylmethane and 20% of the 2,4'-isomer containing 400 ppm hydrogen chloride to give a product of viscosity 35.5 cps. On heating this pale straw coloured material at 80° C for 360 hours resulted in a fall in isocyanate content from 29.45% to 28.2% showing the high thermal stability of this product. The hydrogen chloride in the additional diisocyanate had acted as deactivator.

EXAMPLE 13

250 parts of pure 4,4'-diisocyanatodiphenylmethane were mixed with 0.28 parts of a 10% wt/volume solution of glycidol (in an inert solvent), the glycidol was equivalent to twice the acidity present in the isocyanate. 1.25 parts of a catalyst as a 0.1% wt./vol. solution in perchloroethylene was added to give a concentration of 5 ppm of catalyst based on diisocyanate. The mixture was then heated at 140° C until the isocyanate value had decreased to 29.5% or just below that figure, in which case the isocyanate value was adjusted to 29.5%.

Several experiments were carried out using different catalysts as shown in the following table and the products all had a final isocyanate value of 29.5%.

Each product was split into three portions (a), (b) and (c).

a. was not deactivated.

b. was deactivated by the addition of 50 ppm of thionyl chloride based on the weight of the isocyanate.

c. was treated at 50° C for 1 hour with 20 parts Filtercel (a siliceous earth) and then filtered.

Samples of (a), (b) and (c) in the case of each catalyst were stored at 80° C for the number of days shown in the table and the isocyanate value determined.

Where the sample had gone solid the isocyanate value could not be satisfactorily determined and such non-deactivated products were in any event completely unsatisfactory on account of their poor heat stability.

| Catalyst | Sample | Dyes at 80° C | Isocyanate value |
|---|---|---|---|
| A ![A structure: phospholene with CH3, =P, C6H5N, C6H5] | a | 5 | Solid |
|  | b | 5 | 28.5 |
|  | c | 5 | 28.0 |
| B ![B structure: phospholene with CH3, P, Cl2, C6H5] | a | 5 | Solid |
|  | b | 5 | 27.4 |
|  | c | 5 | 27.8 |
| C ![C structure: phospholene with CH3, P, C6H5] | a | 10 | Solid |
|  | b | 10 | 27.3 |
|  | c | 10 | 27.0 |
| D ![D structure: phospholene with CH3, =P, Cl2, C2H5] | a | 5 | 27.4 |
|  | b | 5 | 28.1 |
|  | c | 5 | 28.6 |

EXAMPLE 14

Pure 4,4'-diisocyanatodiphenylmethane (250 parts) was treated with epichlorohydrin (144 ppm) equivalent to twice the acidity present and 1-phenyl-3-methyl-2-phospholene-1-oxide (5ppm). The mixture was heated at 100° C for 5 hours when a water white product of isocyanate content 26.9% was obtained. More diisocyanate was added to adjust isocyanate content fo 29.5%. The product had a dimer content of 1.29%. On heating a sample in an oven at 80° C this product was a solid within 5 days. A second sample deactivated by adding 50 ppm of thionyl chloride had an isocyanate content of 28.2% after heating under identical conditions for 5 days.

We claim:

1. A process for the conversion of from 3% to 35% of the isocyanate groups in a refined aromatic polyisocyanate having two or more isocyanate groups, into carbodiimide groups which comprises heating said isocyanate with a catalyst of the formula:

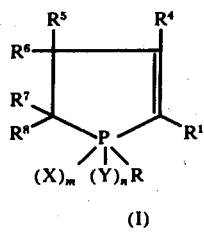    or    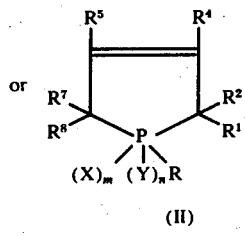

(I)            (II)

wherein R is phenyl, benzyl or ethyl, $R^1$, $R^2$, $R^5$, $R^6$, $R^7$ and $R^8$ are hydrogen, $R^4$ is methyl, X and Y may be chlorine or bromine or X and Y taken together may represent the divalent atoms =O or =S or the divalent radical =N aryl, m and n represent 0 or 1 and are the same in any one compound, followed by deactivation of the catalyst by adsorption on a substrate or by addition of one or more of the halides of hydrogen, phosphorus or tin or an oxyhalide of phosphorus or sulphur.

2. A process as claimed in claim 1 wherein the catalyst is deactivated by the addition of one or more of the halides of hydrogen, phosphorus or tin or an oxyhalide of phosphorus or sulphur.

3. A process as claimed in claim 1 wherein the catalyst is deactivated by adsorption on a substrate followed by removal of the substrate.

4. A process as claimed in claim 1 wherein X and Y taken together represent a divalent oxygen atom.

5. A process as claimed in claim 4 wherein the catalyst is 1-phenyl-3-methyl phospholene oxide.

6. A process as claimed in claim 1 wherein the catalyst is used in an amount of from 1 ppm to 100 ppm on the weight of the isocyanate.

7. A process as claimed in claim 6 wherein the catalyst is used in an amount of from 1 to 25 ppm on the weight of the isocyanate.

8. A process as claimed in claim 7 wherein the amount of catalyst is from 1 to 10 ppm.

9. A process as claimed in claim 1 wherein the isocyanate is a diphenylmethane diisocyanate.

10. A process as claimed in claim 1 wherein at least a proportion of the carbodiimide groups react with further isocyanate groups in the refined organic isocyanate on standing to form uretonimine groups.

11. A process as claimed in claim 1 wherein the conversion is carried out at a temperature below 150° C.

12. A process as claimed in claim 11 wherein the temperature is from 80° C to 140° C.

13. A process as claimed in claim 2 wherein deactivation of the catalyst is carried out by the addition of from one to thirty moles of a deactivating agent as claimed in claim 2.

14. A process as claimed in claim 2 wherein the deactivating agent is thionyl chloride.

15. A process as claimed in claim 3 wherein the catalyst is deactivated by absorption on a siliceous earth substrate.

16. A process as claimed in claim 1 wherein conversion of isocyanate groups is carried out beyond the desired level of conversion and the product blended with a further amount of refined isocyanate to give a product having the desired number of unconverted isocyanate groups.

17. Process as claimed in claim 1 wherein an acid acceptor is incorporated in the reaction mixture.

18. Process as claimed in claim 17 wherein the acid acceptor is a 1,2-epoxide.

19. Process as claimed in claim 17 wherein the acid acceptor is used in an amount of at least one equivalent for each gram molecule of acidity in the isocyanate.

* * * * *